US008062669B2

(12) United States Patent
Aboubakar et al.

(10) Patent No.: US 8,062,669 B2
(45) Date of Patent: Nov. 22, 2011

(54) VECTORIZATION SYSTEM COMPRISING NANOPARTICLES OF HOMOGENOUS SIZE OF AT LEAST ONE POLYMER AND AT LEAST ONE POSITIVELY CHARGED POLYSACCHARIDE AND METHOD FOR THE PREPARATION THEREOF

(75) Inventors: Malam Aboubakar, Lillie (FR); Andrei Maksimenko, Paris (FR); Christine Chaumont, Paris (FR); Valerie Polard, Alfortville (FR)

(73) Assignee: Bioalliance Pharma (FR)

( * ) Notice: Subject to any disclaimer, the term of this patent is extended or adjusted under 35 U.S.C. 154(b) by 409 days.

(21) Appl. No.: 11/014,156

(22) Filed: Dec. 16, 2004
(Under 37 CFR 1.47)

(65) Prior Publication Data
US 2006/0134220 A1 Jun. 22, 2006

Related U.S. Application Data

(63) Continuation of application No. PCT/FR03/01909, filed on Jun. 20, 2003.

(30) Foreign Application Priority Data

Jun. 20, 2002 (FR) ...................................... 02 07668

(51) Int. Cl.
*A61K 9/14* (2006.01)
*A61K 48/00* (2006.01)
(52) U.S. Cl. ........................ 424/489; 977/906; 514/44 R
(58) Field of Classification Search ........................ None
See application file for complete search history.

(56) References Cited

U.S. PATENT DOCUMENTS

| | | | |
|---|---|---|---|
| 3,632,754 A | | 1/1972 | Balassa et al. |
| 4,474,769 A | | 10/1984 | Smith |
| 4,913,908 A | | 4/1990 | Couvreur et al. |
| 5,830,883 A | * | 11/1998 | Block et al. ..................... 514/55 |

FOREIGN PATENT DOCUMENTS

| | | | |
|---|---|---|---|
| FR | 2 649 321 | | 1/1991 |
| FR | 2 649 321 A1 | | 1/1991 |
| FR | 2 724 935 | | 3/1996 |
| FR | 2 724 935 A1 | | 3/1996 |
| WO | WO 96/24377 | | 8/1996 |
| WO | WO99/43359 | * | 9/1999 |
| WO | WO 99/43359 | | 9/1999 |

OTHER PUBLICATIONS

Yang et al (Colloid Polym. Sci., 2000. 278: 285-292).*
Lee et al. (J. Pharm. Sciences, Jul. 2000. vol. 89, No. 7: 850-866).*
Gombotz et al. (Bioconjugate Chem. 1995, 6: 332-351).*
Couvreur et al (J Pharm Pharmacol. May 1979; 31(5): 331-332).*
Schroeder et al. (Peptides 1998. 19(4): 777-780).*
Vijayanathan et al. (Biochemistry. Dec. 3, 2002, 41(48): 14085-14094).*
Hans et al. (Current Opinion in Solid State and Materials Science. 2002; 6: 319-327).*
Cui et al. (Journal of Controlled Release. 2001; 75: 409-419, published online Jul. 30, 2001).*
Hu et al. (Biomaterials. 2002; 23: 3193-3201, available online Mar. 19, 2002).*
P. Couvreur et al., "Polycyanoacrylate nanocapsules as potential lysosomotropic carriers: preparation, morphological and sorptive properties", J. Pharm. Pharmacol., (1979), vol. 31, pp. 331 and 332.
S.C. Yang et al., "Formation of positively charged poly(butyl cyanoacrylate) nanoparticles stabilized with chitosan", Colloid Polym Sci., (2000), vol. 278, pp. 285-292.
H.-P. Zobel et al., "Cationic Polyhexylcyanoacrylate Nanoparticles as Carriers for Antisense Oligonucleotides:", Antisense & Nucleic Acid Drug Development, (1997) vol. 7, pp. 483-493.
Olivier Zelphati et al., "Liposomes as a carrier for intracellular delivery of antisense oligonucleotides: a real or magic bullet?" Journal of Controlled Release, vol. 41, (1996), pp. 99-119.
James M. Wilson et al., Correction of CD18-Deficient Lymphocytes by Retrovirus-Mediated Gene Transfer, Science, vol. 248, Jun. 1990, pp. 1413-1414.
George Y. Wu et al., "Receptor-mediated in Vitro Gene Transformation by a Soluble DNA Carrier System" , The Journal of Biological Chemistry, vol. 262, No. 10, Issue of Apr. 5, 1987, pp. 4429-4432.
Mary X. Tang et al., "In Vitro Gene Delivery by Degraded Polyamidoamine Dendrimers", Bioconjugate Chem., (1966), vol. 7, pp. 703-714.
Inder M. Verma et al., "Gene therapy-promises, problems and prospects", Nature, (Sep. 18, 1997), vol. 389, pp. 239-242.
Simon C.W. Richardson et al., Potential of low molecular mass chitosan as a DNA delivery system: biocompatibility, body distribution and ability to complex and protect DNA, International Journal of Pharmaceutics, vol. 178, (1999), pp. 231-243.
C.K. Rha et al., "Novel Applications of Chitosan", Hemisphere Publishing, Washington, (1984), pp. 285-311.
Jean-Serge Remy et al., "Gene transfer with lipoosermines and polyethylenimines", Advanced Drug Delivery Reviews; (1998), vol. 30, pp. 85-95.
Pilar Calvo et al., "Chitosan and Chitosan/Ethylene Oxide-Propylene Oxide Block Copolymer Nanoparticles as Novel Carriers for Proteins and Vaccines", Pharmaceutical Research, (1997), vol. 14, No. 10, pp. 1431-1436.
Russell J. Mumper et al., "Polyvinyl Derivatives as Novel Interactive Polymers for Controlled Gene Delivery to Muscle", Pharmaceutical Research, (1996), vol. 13. No. 5, pp. 701-709.
Richard A. Morgan et al., "Human Gene Therapy", Annu. Rev. Biochem., (1993), vol. 62, pp. 191-217.

(Continued)

*Primary Examiner* — Scott Long
(74) *Attorney, Agent, or Firm* — DLA Piper LLP (US)

(57) ABSTRACT

A vectorization and delivery system of therapeutic or diagnostic substances including (i) at least one polymer and (ii) at least one nontoxic positively charged polysaccharide, the nanoparticles having a substantially homogeneous distribution of size.

18 Claims, 11 Drawing Sheets

OTHER PUBLICATIONS

Fred D. Ledley, "Non-viral gene therapy", Current Opinion in Biotechnology, (1994), vol. 5, pp. 626-636.

D.D. Lasic et al., "Liposomes in gene therapy", Advanced Drug Delivery Reviews, (1996), vol. 20, pp. 221-266.

Jan Knapczyk et al. "Pharmaceutical Dosage Forms With Chitosan", Elsevier Applied Science, London, (1984), pp. 665-669.

Alexander V. Kabanov et al., "Micelles of amphiphilic block copolymers as vehicles for drug delivery", BioAlliance Pharma, (Date?), pp. 347-376.

Shigehiro Hirano et al., "Chitosan: A Biocompatible Material for Oral and Intravenous Administrations", Plenum Press, NY (1990), pp. 283.

Ira W. Hillyard et al., "Antacid and Antiulcer Properties of the Polysaccharide Chitosan in the Rat", P.S.E.B.M., (1964), vol. 115, pp. 1108-1112.

Ellen F. Fynan et al., "DNA vaccines: Protective immunizations by parenteral, mucosal, and gene-gun inoculations", Proc. Natl. Acad. Sci. USA, Immunology, (Dec. 1993), vol. 90, pp. 11478-11482.

G. Fradet et al., "Evaluation of Chitosan as a New Hemostatic Agent: In Vitro and In Vivo Experiments", Plenum Press, NY, (1986), pp. 443-451.

Rocio Fernandez-Urrusuno et al., "Enhancement of Nasal Absorption of Insulin Using Chitosan Nanoparticles", Pharmaceutical Research, (1999). vol. 16, No. 10.

Philip L. Felgner, "Particulate systems and polymers for in vitro and in vivo delivery of polynucleotides", Advanced Drug Delivery Reviews, (1990), vol. 5, pp. 163-187.

Patrick Erbacher el al., "Chitosan-Based Vector/DNA Complexes for Gene Delivery; Biophysical Characteristics and Transfection Ability" Pharmaceutical Research, (1998), vol. 15. No. 9, pp. 1332-1339.

J.T. Douglas et al., "Targeted gene therapy", Tumor Targeting, (1995), vol. 1, pp. 67-84.

S.T. Crooke, "Delivery of Oligonucleotides and Polynucleotides", Journal of Drug Targeting, (1995), vol. 3, pp. 185-190.

Christine Chavany et al., "Polyalkylcyanoacrylate Nanoparticles as Polymeric Carriers for Antisense Oligonucleotides", Pharmaceutical Research, (1992), vol. 9, No. 4, pp. 441-449.

Thomas Chandy et al., "Chitosan—As a Biomaterial", Biomat., Art. Cells, Art. Org., (1990), vol. 18 (1), pp. 1-24.

Otmane Boussif et al., "A versatile vector for gene and oligonucleotide transfer into cells in culture and In vivo: Polyethylenimine", Proc. Natl. Acad. Sci., USA,, Biochemistry, (Aug. 1995), vol. 92, pp. 7297-7301.

Jean-Paul Behr et al., Efficient gene transfer into mammalian primary endocrine cells with lipopolyamine-coated DNA, Proc. Natl. Acad. Sci. USA, (Sep. 1989), vol. 86, pp. 6982-6986.

P. Calvo et al., "Oligonucleotide—Chitosan Nanoparticles As New Gene Therapy Vector", Proc. 2$^{nd}$ World Meeting APG1/APV, Paris, (May 25/28, 1998), pp. 111-1112.

Kobayashi, T. et al., "Effect of Chitosan on Serum and Liver Cholesterol Levels in Cholesterol-Fed Rats," *Nutrition Reports International*, Mar. 1979, vol. 19, No. 3, pp. 327-334.

Kreuter, J., "Nanoparticles," *J. Colloidal Drug Delivery Systems*, Marcel Decker, New York, 1994, pp. 219-342.

Struszczyk, H. et al., "Biodegradability of Chitosan Fibres," *Elsevier Applied Science*, 1991, pp. 580-585.

Roberts, G.A.F., "Structure of Chitin and Chitosan," *Chitin Chemistry*, G.A.F. Roberts, ed., Houndsmills, England, Macmillan, 1992, Chapter 1, pp. 1-53.

Roberts, G.A.F., "Solubility and Solution Behavior of Chitin and Chitosan," *Chitin Chemistry*, G.A.F. Roberts, ed., Houndsmills, England, Macmillan, 1992, Chapter 6, pp. 274-329.

* cited by examiner

VECTORIZATION SYSTEM COMPRISING NANOPARTICLES OF HOMOGENOUS SIZE OF AT LEAST ONE POLYMER AND AT LEAST ONE POSITIVELY CHARGED POLYSACCHARIDE AND METHOD FOR THE PREPARATION THEREOF

RELATED APPLICATION

This is a continuation of International Application No. PCT/FR03/01909, with an international filing date of Jun. 20, 2003 (WO 2004/000287, published Dec. 31, 2003), which is based on French Patent Application No. 02/07668, filed Jun. 20, 2002.

TECHNICAL FIELD

This disclosure pertains to the delivery of active principles used especially in the field of pharmaceuticals for preventive, curative or diagnostic purposes. The disclosure more specifically relates to a delivery and vectorization system of substances of interest.

BACKGROUND

The development of new systems for the delivery or release of active principles has as a first object the controlled delivery of an active agent, especially a pharmacological agent, to its site of action at a therapeutically optimal rate and dosage (J. Kreuter, 1994). The improvement of the therapeutic index can be obtained by modulation of the distribution of the active principle in the organism. The association of the active principle with the delivery system makes possible its specific delivery to the site of action or of its controlled release after targeting the site of action. The reduction in the amount of active principle in the compartments in which its presence is not desirable makes it possible to increase the efficacy of the active principle, to reduce its toxic side effects and even to modify or restore its activity.

One of the major issues of delivery is its application to molecular biology and, most particularly, its application to active principles such as deoxyribonucleic acids (DNAs), oligodeoxynucleotides (ODNs), peptides, proteins—all negatively charged. The molecular biology bases in genetic diseases makes it possible to modulate or replace a dysfunctional gene. The development of gene therapy as routine in clinical practice is dependent on the possibility of repeated administration via the systemic route, the capacity to reach a target and to effectively transfect cells in vivo (Felgner, 1990; Kabanov and Alakhov, 1993; Crook, 1995; Douglas and Curiel, 1995; Lasic and Templeton, 1996) as well as the possibility of fabricating vectors which will be capable of being adapted to an industrial scale. The techniques of in vitro transfection used to date, such as electroporation and co-precipitation of DNA with calcium phosphate, are approaches the application of which in vivo would appear to be difficult (Fynan et al., 1993).

The systems for in vivo transfection take into account the natural negative charge of DNAs and ODNs. These are either viral systems (Morgan and Anderson, 1993) or nonviral constructions such as cationic lipids (Ledley, 1994; Zelphati and Szoka, 1996). The viral vectors are very effective in terms of in vitro transfection, but they have limitations in vivo because of their immunogenicity (Wilson et al., 1990; Douglas and Curiel, 1995; Verma and Somia, 1997). Among the nonviral vectors, the cationic lipids such as Transfectam (Behr et al., 1989) have good transfection properties, but their application in vivo is limited by their toxicity, the activation of the complement and their notable tropism for the liver and the lungs.

Since the studies carried out with poly(1-lysine) at the end of the 1980s (Wu and Wu, 1987), many cationic polymers have been studied as nonviral transfection vectors. These vectors include polyethyleneimine (Boussif et al., 1995; Remy et al., 1998), polybrene (Mumper et al., 1996) and the dendrimers of poly(amidoamine) (PAMAM) (Tang et al., 1996).

Until now, the efficacy of transfection with polymers is relatively low and many of these cationic polymers have exhibited a relative toxicity with low potentials of repeated administration via the intravenous route. The polymers used directly with the active principles notably DNA are limited by their transfection efficacy and consume a large amount of active principle and thus require the use of a large amount of polymer, which is itself toxic. The colloidal systems used for the delivery notably of genes in vivo use smaller amounts of polymer and active principle.

The colloidal delivery systems of active principles comprise the liposomes, microemulsions, nanocapsules, nanospheres, microparticles and nanoparticles. Nanoparticles have advantages of targeting, modulation of distribution and flexibility of formulation and have a polymer structure which can be designed and implemented in a manner adapted to the goal. They have been found to be promising for obtaining a better therapeutic index in the sense defined above because of their aptitude to ensure a controlled release, a specific delivery to the site of action or targeted delivery, enabling both an augmentation of the efficacy and a reduction in the toxic side effects at the level of the other organs.

Among these, the poly(alkyl cyanoacrylates) described in EP-B-0 007 895 (U.S. Pat. No. 4,329,332 and U.S. Pat. No. 4,489,055) and EP-B-0 064 967 (U.S. Pat. No. 4,913,908) are particularly interesting because their bioerosion takes place rapidly in relation to other biodegradable polymers and unfolds over durations compatible with therapeutic and diagnostic applications. The nanoparticles are colloidal vectors the diameter of which ranges between 10 nm and 1000 nm. These particles are formed by macromolecules in which the biologically active substance is trapped, encapsulated or adsorbed at the surface. Nanoparticles or nanospheres are described by Birrenbach and Speiser (1976) in terms of nanopellets and nanocapsules and qualified by Kreuter and Speiser (1976) as adjuvants and delivery systems of active substances by Kreuter (1983).

With the goal of increasing the stability of the oligonucleotides, of increasing their penetration into the cells and avoiding nonspecific distribution, the use of particular vectors, like nanoparticles, is considered to be one of the most promising approaches. However, their use has been limited by the toxicity of the substance used to affix the active principle to the nanoparticle.

The polymer nanoparticles that have been subjected to the greatest amount of research are the polyisohexylcyanoacrylates (PIHCA). However, as nanoparticles having a negative surface charge, a cationic copolymer (diethylaminoethyl (DEAE) dextran) or a cationic hydrophobic detergent (cetyl trimethyl ammonium bromide (CTAB)) were combined with polyalkylcyanoacrylates (PACA) to facilitate association of ODNs by formation of ion pairs on the nanoparticles. Thus, the ODNs were effectively associated with the PACA nanoparticles containing a hydrophobic cation such as CTAB (cetyl trimethyl ammonium bromide, Chavany et al., 1992). Since CTAB has toxicity problems, Zobel et al., 1987 replaced the CTAB with DEAE dextran which was introduced into the polymerization medium prior to formation of the nanospheres. DEAE dextran was also found to be toxic.

A desirable nanoparticle vector for delivery of active principles such as DNAs, ODNs, peptides and proteins should be:

capable of forming a complex with the molecule of interest taking into account its physicochemical characteristics and the substance selected for affixing the active principle must be adapted to the charge and the toxicity data, capable of protecting the active principle from degradation during its transport in the circulating blood, biocompatible (nontoxic, nonimmunogenic and preferably biodegradable), capable of delivering the active principle to the level of the target tissue in sufficient quantity, and capable of targeting specifically a cell type.

SUMMARY

We provide a vectorization and delivery system of therapeutic or diagnostic substances comprising (i) at least one polymer and (ii) at least one nontoxic positively charged polysaccharide, the nanoparticles having a substantially homogeneous distribution of size.

We also provide a method for preparing nanoparticles having a substantially homogeneous distribution of size and including polymerization at an acid pH higher than 1 of monomers in the presence of the positively charged polysaccharide to obtain a suspension of nanoparticles.

BRIEF DESCRIPTION OF THE DRAWINGS

Other advantages and characteristics will become apparent from the examples below concerning the preparation of nanoparticles and their capacity to transport oligonucleotides, and in which reference will be made to the attached drawings in which.

DETAILED DESCRIPTION

Figure 1:
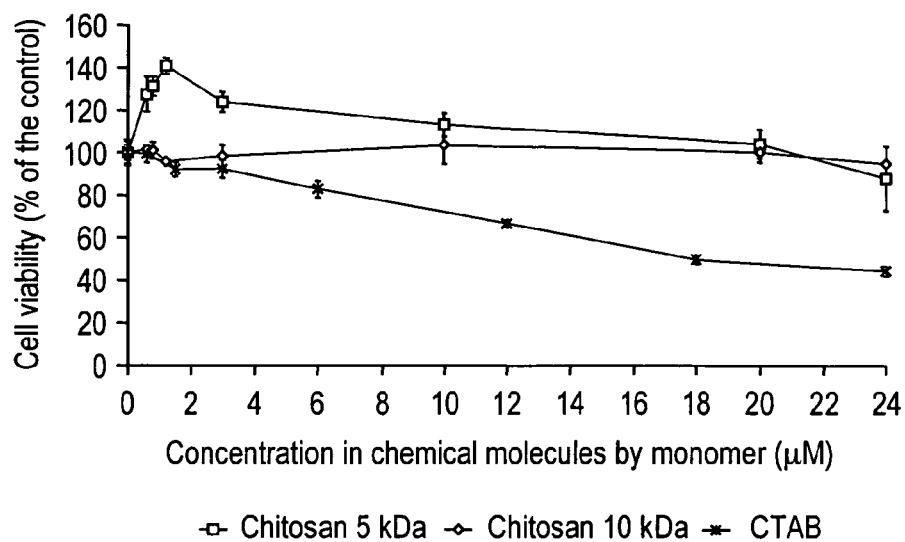
FIG. 1 is a graph showing the toxicity of the different preparations on NIH 3T3 EWS-Fli1 cells.
Figure 2:
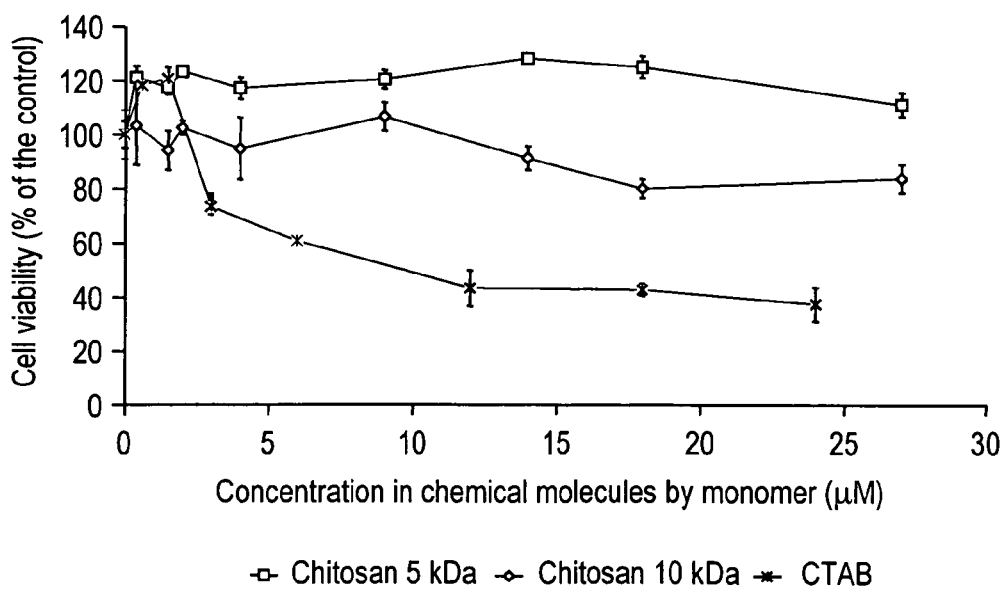
FIG. 2 is a graph showing the toxicity of the different preparation on NIH 3T3 cells.
Figure 3:
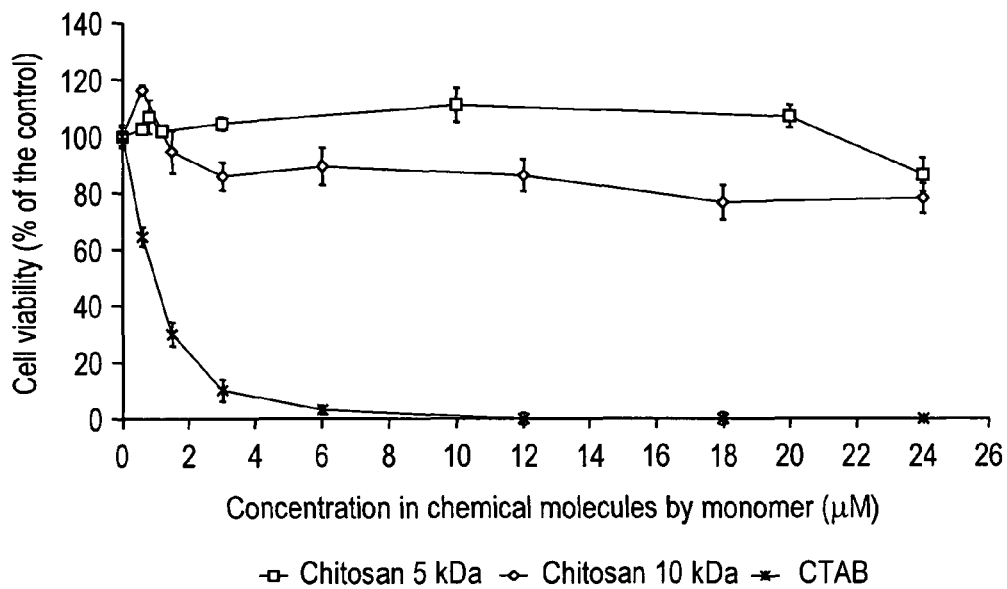
FIG. 3 is a graph showing the toxicity of the different preparations on IW 35 cells.
Figure 4:
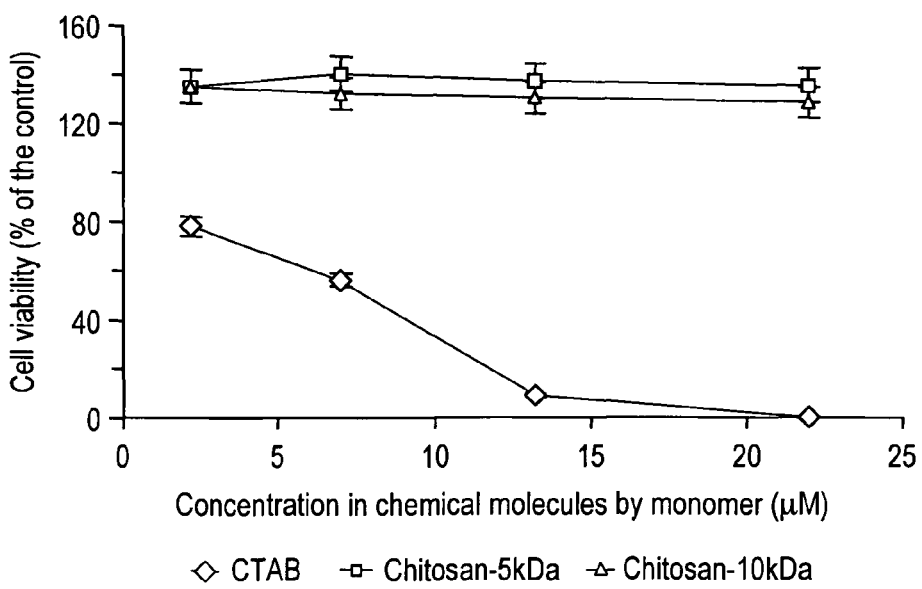
FIG. 4 is a graph showing the toxicity of the different preparations on CEM 4FX cells.

We provide a vectorization and delivery system of substances of therapeutic or diagnostic interest, of the type constituted of nanoparticles, characterized in that the nanoparticles have a homogeneous size distribution and comprise (i) at least one polymer and (ii) at least one nontoxic positively charged polysaccharide.

The substances of interest are incorporated or adsorbed at the level of the nanoparticles. The vectorization and delivery system is particularly suitable for anionic substances of interest or those comprising an anionic region. The polymer is preferably a poly(alkyl cyanoacrylate) in which the linear or branched alkyl group comprises from 1 to 12 carbon atoms.

The polysaccharide(s) entering into the composition of the nanoparticles of the invention is(are) nontoxic, unlike the substances taught by the prior art such as CTAB or DEAE dextran.

Thus, the system most particularly pertains to a positively charged polysaccharide which is linear. It is preferably a derivative of chitin and most preferably of chitosan or its derivatives as long as they are positively charged.

Chitin is the second most abundant polysaccharide in nature after cellulose. The skeleton is composed of β1-4- glucosamine sugars with a high degree of N-acetylation. This structure is close to that of cellulose, the difference being the replacement of the hydroxyl functional group by an amino group (Roberts, 1992). These polycationic biopolymers constitute the exoskeleton of crustaceans and insects, but they are also present in certain mushrooms (Roberts, 1992). Chitosan, the principal derivative of chitin, is usually obtained by alkaline deacetylation. The two types of polymers (chitin and chitosan) are differentiated by their solubility or insolubility in a dilute acid solution (Roberts, 1992).

Chitosan has been the object of extensive studies in the pharmaceutical and biomedical fields because of its favorable biological properties such as its nontoxicity (Knapczyk et al., 1984), its biocompatibility (Candy and Sharma, 1990; Hirano et al., 1991) and its biodegradability (Struszczyk et al., 1991). In the medical field, chitosan has been described as possessing interesting pharmacological properties such as its cholesterol-reducing activity (Kobayashi et al., 1979), its cicatrizing properties (Balassa and Grove, 1972) and its antacid and antiulcer activities (Hillyard et al., 1964). Moreover, its polycationic nature confers on it the capacity to strongly associate itself with mammal cells thereby enabling potentialities of use for its hemostatic activity (Fradet et al., 1986) and its spermicidal activity (Smith, 1984).

The molecular weight of the polysaccharides was determined to obtain homogeneous nanoparticles of a size sufficiently small to facilitate their administration. Thus, these polysaccharides, and most particularly chitosan or its derivatives, have a molecular mass lower than about 100,000 Da, preferably lower than about 30,000 Da. Chitosan of 5,000, 10,000 and 30,000 Da was synthesized in the examples.

An example of chitosan derivatives is PEGylated chitosan, i.e., chitosan to which was grafted polyethylene glycol or chitosan functionalized with folic acid for targeting cancer cells.

The delivery and vectorization system makes it possible to modulate the delivery of the substance of interest as a function of the amount of positively charged polysaccharide in the nanoparticles. This charge modulation was impossible in the prior art because of the toxicity of the detergents like CTAB or the copolymers like DEAE dextran. Thus, the amount of polysaccharide comprises between about 0.1 and about 1% in relation to the amount of polymer.

The nanoparticles can also comprise at least one compound capable of complexing the substance of interest. This is, for example, a compound described in FR 2 775 435. The compound capable of complexing the active substance is advantageously a cyclic oligosaccharide, preferably a neutral or charged native cyclodextrin which is branched or polymerized or chemically modified. It can be a cyclodextrin modified chemically by substitution of one or more hydroxypropyls by alkyl, aryl, arylalkyl or glycoside groups, or by esterification with alcohols or aliphatic acids.

The vectorization and delivery system is most particularly suitable for anionic substances of interest or substances comprising an anionic region. Thus, it can be a question of substances of interest that are not charged or are charged positively, but modified to confer in totality or in part a negative charge enabling their association with the positively charged nanoparticles. The substance of interest is affixed on the nanoparticles in a covalent or noncovalent manner.

Examples include, but are not limited to, DNA or oligodeoxyribonucleotides or oligoribonucleotides notably antisense substances or interfering RNA (siRNA) or peptides, polypeptides or proteins and chemical compounds. Nucleic acids are anionic substances, but certain peptides, polypeptides and proteins are also anionic or comprise a negatively charged region. Examples of substances of interest capable of being associated with the nanoparticles include, but are not limited to, insulin, calcitonin and triptorelin at pH greater than their pHi.

The nanoparticles have a homogeneous diameter between about 10 and about 300 nm as a function of the molecular weight of chitosan and the concentration used. The nanoparticles can be prepared by emulsion polymerization techniques (Couvreur et al., 1979) of the type described in FR 2 775 435 as well as in the experimental part below.

We also provide a method for the preparation of these nanoparticles comprising polymerization at an acid pH greater than that of one of the monomers in the presence of the positively charged polysaccharide.

The polysaccharide is preferably added at the beginning of polymerization and the acid pH is preferably greater than about 3. According to an especially preferred aspect, polymerization is performed in the presence of a polymerization retarder such as $SO_2$ or hydroquinone, which affixes on the OH groups of the aqueous polymerization medium or the polysaccharide.

By means of the above process, a suspension of nanoparticles of polymer and polysaccharide is obtained, the positive charge of which is dependent on the amount of polysaccharide added. The amount of polysaccharide is advantageously between about 0.1 and about 1% in relation to the weight of the suspension.

The anionic substance of interest can be added at any moment of the above process. In fact, polymerization at an acid pH, but with a value greater than about 1 makes it possible to introduce even at the beginning of the process substances of interest sensitive to excessively acid pH values. The amount of substance of interest is advantageously between about 0.5 and about 50% in relation to the weight of the suspension.

The following process can be cited as a specific example:

100 µl of polyisohexylcyanoacrylate containing 0 to 20,000 ppm of $SO_2$ was added to a solution of citric acid (with a pH ranging from 1 to 5) containing 1% of nonionic surface-active agent, poloxamer 188, and optionally 0.5% of cyclodextrin and containing 0.2% of chitosan of low molecular weight (5000 or 10,000 Da).

It should be remembered that the use of chitosan to obtain positively charged nanoparticles was already described in Yang S. C. et al., 2000. However, the process of the prior art is performed at a very acid pH (pH 1) of the polymerization medium at which the active principles are not stable.

In this method, the pH of the polymerization medium is between about 2.5 and about 5, at which the active principles are stable. Furthermore, the method described by Yang S. C. et al. employs a chitosan of molecular weight higher than 30,000 Da. The use of chitosan of molecular weight greater than 10,000 Da exhibits toxicity (Richardson S. C. W. et al., 1999). In contrast, the nanoparticles comprise chitosan of low molecular weight (5000 and 10,000 Da), which makes it possible to obtain nanoparticles having a mono-disperse size distribution and thus greater tolerance.

The method described by Yang S. C. et al. is limited by the concentration of chitosan present in the polymerization medium because at a concentration of chitosan lower than 0.25% the resultant nanoparticles are unstable. This method produces stable nanoparticles at concentrations of chitosan lower than 0.25%.

The vectorization and delivery system of a substance of interest can be in the form of a suspension of nanoparticles or in the form of a lyophilizate of nanoparticles. It allow intravenous, oral or local administration without denaturing the substance of interest.

Example I

Comparison of Toxicity of Chitosan of Different Molecular Weights and CTAB on Different Cell Lines 1. Materials and Methods The NIH 3T3 and NIH 3T3 EWS-Fli-1 (adherent cells) were sown on 6-well plates at 100,000 cells per well in their culture medium without puromycin and the IW35 cells (cells in suspension) in 12-well plates at the rate of 750,000 cells per well. Other cells in suspension CEM 4FX were also tested. They were sown at 10,000 cells per well in 96-well plates.

For the first two cell types, the cells were sown 24 hours prior to their transfection. The medium was then eliminated and 100 µl of solution of the complex to be tested was brought into contact with the cells in 900 µl of medium.

Different concentrations of CTAB and chitosan of various molecular weight were tested.

Two controls were used and corresponded to the cells in the culture medium on the one hand and in the culture medium containing 100 µl of NaCl 150 mM on the other hand. After 24 hours of incubation, the measurements of cytotoxicity were performed by a test measuring the activity of the mitochondrial dehydrogenase enzymes of the living cells by oxidation of MTT (3-(4,5-dimethyl thiazol-2-yl)-2,5-diphenyl tetrazolium bromide; SIGMA) in formazan. The amount of formazan produced is directly proportional to the number of metabolically active live cells. The cells were washed with PBS and 1 ml of the medium was added. The cells were then incubated at 37° C. with 100 µl of a solution of MTT (5 mg/ml in PBS) for 3 hours. 1 ml of a lysis solution (10% SDS, 10 mM Tris) was then added to each well. The cells were incubated at 37° C. overnight. The medium was homogenized and the optical density was read at 560 nm (Dynatech MRX).

2. Results

The toxicity of the different preparations on the different cells (NIH 3T3, NIH 3T3 EWS-Fli1, IW 35 and CEM 4FX) is shown as a function of the concentration of positively charged molecules (FIGS. 1-4). For the NIH 3T3 cells with and without EWS-Fli1 (adherent cells) (FIGS. 1-2), there can be seen a notable toxicity of CTAB compared to chitosan of 5 or 10 kDa. Furthermore, chitosan 5 kDa is not toxic and stimulates the cellular viability.

For the cells in suspension (IW35 and CEM 4FX) (FIGS. 3 and 4), the two types of chitosan 5 and 10 kDa do not exhibit notable toxicity compared to CTAB which exhibits elevated toxicity at low concentrations.

Example II

Formulation of Positively Charged Nanoparticles in the Presence of Chitosan of Different Molecular Weights The nanoparticles were prepared by the emulsion polymerization technique (Couvreur et al., 1979). 100 ml of polyisohexylcyanoacrylate containing $SO_2$ (MONOREX® polyisohexyl cyanoacrylate, BioAlliance Pharma) was added to a solution of citric acid diluted to pH=3 containing 1% of nonionic surface-active agent, poloxamer 188, containing or not containing 0.5% cyclodextrin and containing 0.2% chitosan of low molecular weight (5,000 or 10,000 Da). The duration of polymerization was 6 hours. After polymerization, the size was determined after dilution of the particles in MilliQ water and the zeta potential was determined after dilution of the particles in NaCl 1 mM. Table 1 below presents the size and the zeta potential of the nanoparticles in relation to the molecular weight of the chitosan.

TABLE 1

| | Diameter (nm) | Standard deviation | Polydispersity index | Zeta potential |
|---|---|---|---|---|
| Chitosan MW 5 kDa nanoparticles | 58 | 16 | 0.025 | +21 |
| Chitosan MW 5-10 kDa nanoparticles | 60 | 15 | 0.065 | +22 |

The diameter of the particles does not vary as a function of the molecular weight of the chitosan. Irrespective of the MW of the chitosan used at the concentration of 0.2%, the resultant nanoparticles were very small and monodisperse as can be seen from the value of the polydispersity index.

The zeta potential of these particles was positive and the charge was independent of the molecular weight of the chitosan.

Example III

Comparison of Toxicity of Nanoparticles Charged with Chitosan and with CTAB

1. Materials and Methods

CEM 4FX cells in suspension were sown at the rate of 10,000 cells per well in 96-well plates. Different concentrations of nanoparticles possessing positive charges from addition of CTAB or chitosan 5 kDa and 10 kDa were tested.

Two controls were used and corresponded to the cells in the culture medium on the one hand and in the culture medium containing 100 µl of NaCl 150 mM on the other hand. After 24 hours of incubation, the measurements of cytotoxicity were performed by a test measuring the activity of the mitochondrial dehydrogenase enzymes of the living cells by oxidation of MTT in formazan. The amount of formazan produced is directly proportional to the number of metabolically active living cells. The cells were washed with PBS and 1 ml of the medium was added. The cells were then incubated at 37° C. with 100 µl of a solution of MTT (5 mg/ml in PBS) for 3 hours. 1 ml of a lysis solution (10% SDS, 10 mM Tris) was then added to each well. The cells were incubated at 37° C. overnight. The medium was homogenized and the optical density was read at 560 nm (Dynatech MRX).

2. Results

Figure 5:
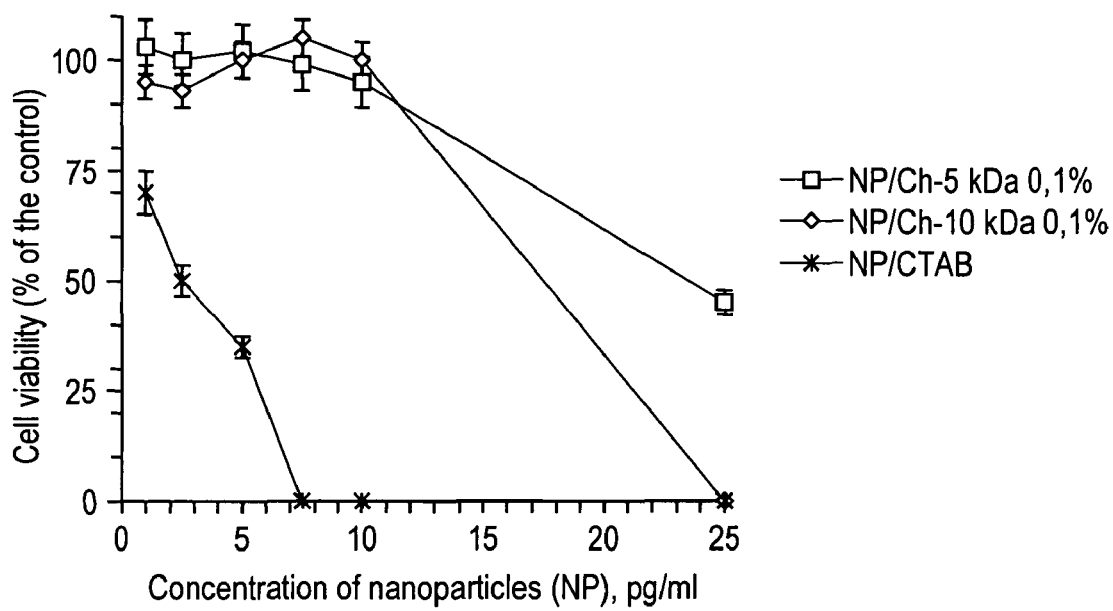
FIG. 5 is a graph showing the toxicity of chitosan 5 kDa and 5-10 kDa nanoparticles and CTAB nanoparticles on CEM4FX cells after 24 h of incubation.

On the CEM 4FX cell line, the nanoparticles of chitosan 5 and 10 kDa only exhibited toxicity starting at 10 µg/ml, whereas the nanoparticles charged with CTAB were toxic beginning at 10 µg/ml (FIG. 5).

Example IV

Formulation of Nanoparticles Charged with Oligonucleotides

The oligonucleotides were negatively charged macromolecules capable of interacting with positively charged surfaces.

We studied the formation of complexes of the chitosan nanoparticles with the antisense EF3008AS oligonucleotides.

The antisense oligonucleotides are nucleic sequences capable of hybridizing selectively with target cell messenger RNAs to inhibit their translation into protein. These oligonucleotides form double-strand regions locally with the target mRNA by interactions of the classic Watson-Crick type.

1. Materials and Methods

The mother solutions of nanoparticles (10 mg/ml) were diluted to the final concentration of 1 mg/ml in Tris-HCl buffer pH=7 at 10 mM in final concentration. The adsorption of the oligonucleotides on the chitosan nanoparticles was performed in 150 mM of NaCl for 30 minutes at ambient temperature after having vortexed the solutions for approximately 30 seconds. The complexes were then incubated for 30 minutes at ambient temperature.

The formation of CTAB-oligonucleotide nanoparticle complexes was performed in the presence of CTAB (at the level of 3 µmoles of CTAB per 5 µg of nanoparticle) and oligonucleotides in 150 mM of NaCl. The oligonucleotides were adsorbed on the CTAB nanoparticles at the end of 2 hours under agitation at ambient temperature. The preparation of the complexes was performed in a final volume of 200 µl.

Different quantities of 30-mer oligonucleotides (EF3008AS) (20, 50, 100, 125, 150 and 200 µg) were mixed with 100 µg of chitosan 5 kDa nanoparticles and chitosan 5-10 kDa nanoparticles.

Figure 6:
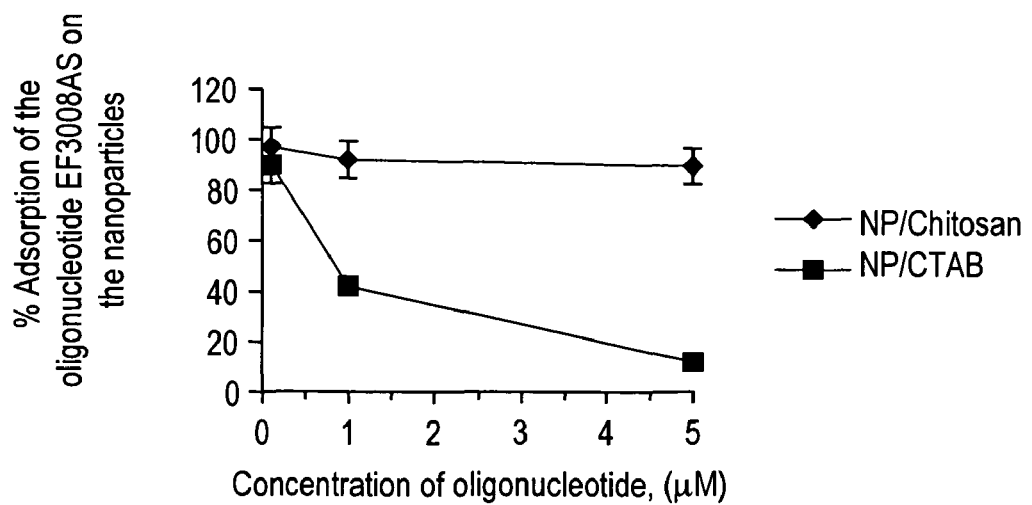
FIG. 6 is a graph showing the adsorption of oligodeoxynucleotide EF3008As on chitosan 5 kDa nanoparticles and CTAB nanoparticles.

The nanoparticles charged with oligonucleotides as well as the oligonucleotides alone were centrifuged at 35,000 rpm (Beckman Optima L80, rotor TW50, 1) for 30 minutes at 4° C. The quantity of oligonucleotide adsorbed on the nanoparticles was calculated by determining the amount of DNA released in the supernatants (FIG. 6).

2. Results

For the oligonucleotide/nanoparticle ratios of 0.2/1 and 0.5/1 there was obtained an adsorption of close to 100% of EF3008AS antisense oligonucleotides on the chitosan 5 kDa nanoparticles. For the chitosan 5-10 kDa nanoparticles, there was obtained an adsorption of 100% for the oligonucleotide/nanoparticle ratio of 0.2/1; the adsorption percentage dropped to 80% at the oligonucleotide/nanoparticle ratio of 0.5/1. For these two oligonucleotide/nanoparticle ratios (0.2/1 and 0.5/1) the adsorption of oligonucleotides on the CTAB nanoparticles reached a maximum of 10%. It is important to note that for an oligonucleotide/nanoparticle ratio of 1/1 there was obtained a percentage of oligonucleotide adsorption of 80% with the chitosan 5 kDa nanoparticles (FIG. 6).

Example V

Study of the Protection of the Oligodeoxynucleotides Adsorbed on the Nanoparticles 1. Materials and Methods The integrity of the oligodeoxynucleotide EF3008AS alone and associated with chitosan nanoparticles was determined in 10% decomplemented neonatal calf serum. At different incubation times, samples of 15 µl were collected, mixed with the same volume of a formamide/water (4/1) solution, 0.01% of bromophenol blue and 0.01% of xylene cyanol and frozen at −20° C. The nanoparticles were degraded by NaOH at pH=12 for 2 hours at 37° C. The oligodeoxynucleotides were then recovered by a double extraction with phenol/chloro-form/isoamyl alcohol (25/24/1) and were then precipitated in 10 volumes of acetone containing 2% of lithium perchlorate for 30 minutes at −20° C.

The oligodeoxynucleotides were then taken up again with 5 ml of formamide/water (4/1) solution, 0.01% of bromophenol blue and 0.01% of xylene cyanol, heated for 5 minutes at 95° C. then put in the freezer. They were analyzed on a denaturing gel at 20% of polyacrylamide, 7M of urea and TBE 1×. The gel was scanned by a photoimager (Storm 840, Molecular Dynamics). The degradation of the oligodeoxynucleotides was quantified by determining the ratio of the signal of the bands corresponding to the intact oligodeoxynucleotides and the degraded oligodeoxynucleotides.

2. Results

Figure 7:
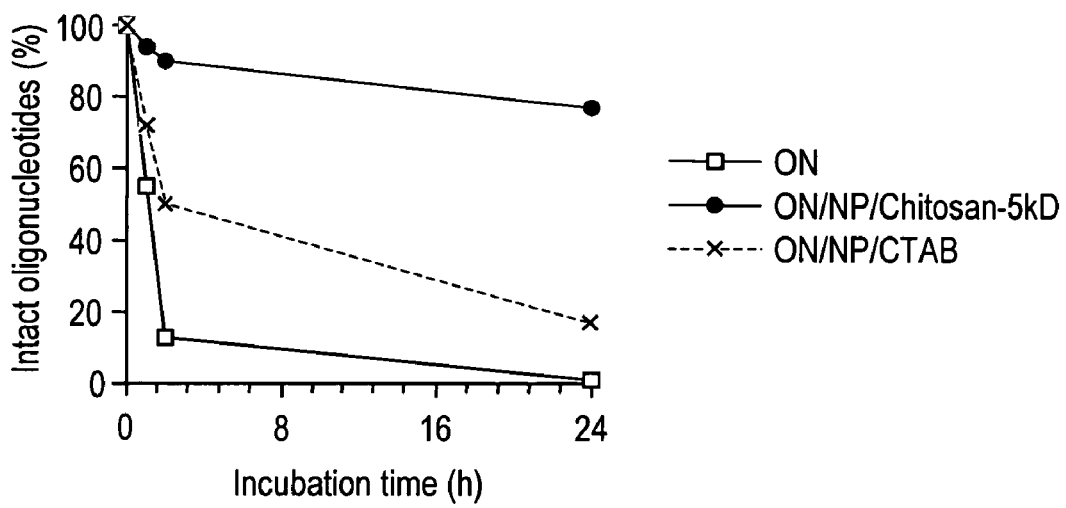
FIG. 7 is a graph showing the stability of the oligonucleotide EF3008AS.
Figure 8A:
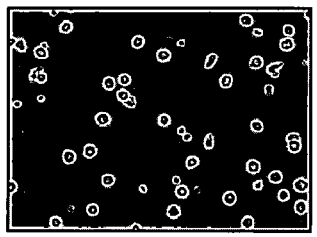
FIG. 8 shows chitosan 5 kDa nanoparticles with oligonucleotide 11 mer (D) and oligonucleotide 7 mer OPC (B) in CEM4FX cells.
Figure 8B:
Figure 8C:
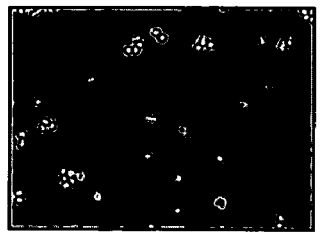
Figure 8D:
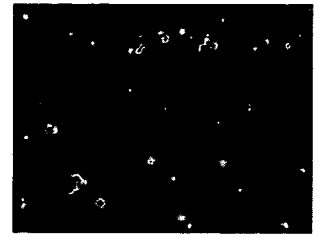

FIG. 7 shows that there is a good protection of 30-mer oligodeoxynucleotides by the chitosan nanoparticles.

Example VI

Transfection of Human Cells by Chitosan Nanoparticles Charged with Oligodeoxynucleotides 1. Materials and Methods a. Preparation of the Cells Human CEM4FX cells were used. 500,000 cells in suspension were sown in 12-well plates (TPP, Suisse) in 850 µl of an RPMI medium containing 10% of fetal calf serum (FCS).

b. Transfection of the Cells

150 µl of the suspension of nanoparticles prepared above was brought into contact with the cells for 24 hours.

c. Fixation of the Cells

The cells were then fixed prior to performing a fluorescence observation. At the end of 24 hours of incubation of the cells in the presence of the nanoparticles, 1 µg of propidium iodide was added to each well which enabled recognition of the dead cells by staining them red.

The cells were then centrifuged at 1000 rpm for 5 minutes. The supernatant was collected and the cells were washed once more with PBS. 200 µl of PBS containing 4% of formaldehyde was then added and the cells were left at ambient temperature for 30 minutes. The cells were then washed twice with PBS 0.1×. Another washing with sterile water was also performed to terminate. 20 µl of polylysine was added at the end. The observation of the cells was performed with a microscope equipped with a filter at 480 nm.

2. Results

Figure 9A:
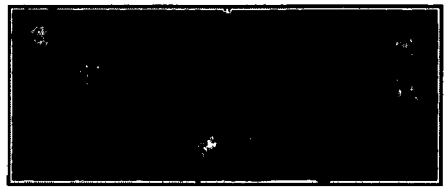
FIG. 9 shows chitosan 5 kDa nanoparticles with oligonucleotide 11 mer Fluo in IW 35 cells.
Figure 9B:
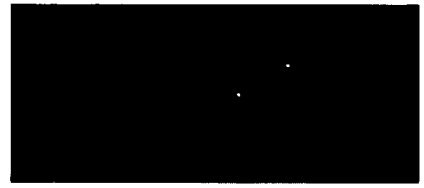
Figure 10A:
FIG. 10 shows chitosan 5 kDa nanoparticles (A) and 5-10 kDa nanoparticles (B) with the oligonucleotide EFAS 30-mer.
Figure 10B:

Each of the observations of the FIGS. 8, 9 and 10 was performed for the two types of oligonucleotides 7 bases and 11 bases.

The cells in the presence of chitosan 5 kDa nanoparticles-oligodeoxynucleotides were very fluorescent and no toxicity was visible. In the presence of the formulation chitosan 5 kDa nanoparticles-Cyd-oligodeoxynucleotides, they were also fluorescent but multiple dead cells were visible.

The formulation chitosan 10 kDa nanoparticles-Cyd-oligodeoxynucleotides also presented good fluorescence but also a slightly higher toxicity than the 5 kDa-Cyd-oligodeoxynucleotides nanoparticles. In the presence of 30 kDa-Cyd-oligodeoxynucleotides nanoparticles the cells were also very fluorescent but the number of dead cells was even higher than in the two preceding cases.

In the case of the cells incubated in the presence of CTAB-Cyd-oligonucleotides, the fluorescence was weak and the toxicity was very high. The complex CTAB-oligodeoxynucleotides did not exhibit any cellular fluorescence.

In the case of the cells incubated in the presence of cytofectin-oligodeoxynucleotides no cellular fluorescence was observed.

Example VII

Transfection in Vitro of NIH-3T3 EWS-Fli1 Cells by Plasmid-Chitosan Nanoparticle Complexes 1. Materials and Methods
   a. Plasmid Coupled to Rhodamine
   10 µg of β-galactosidase plasmid was tagged with a red fluorophore Oregon Green 546 (ULYSIS® Nucleic Acid Labeling Kits, Molecular Probes). This fluorophore yields a red fluorescence (Ex/Em est 555/570).

1 µg of labeled plasmid and 3 µg of unlabeled plasmid were mixed with chitosan nanoparticles in 200 µl of NaCl at 15 µM and vortexed then incubated for 30 minutes at ambient temperature. The adherent NIH-3T3 EWS-Fli1 cells were sown in 6-well plates (TPP, Suisse) 24 hours prior to transfection so as to reach 70% confluence.

Figure 11A:
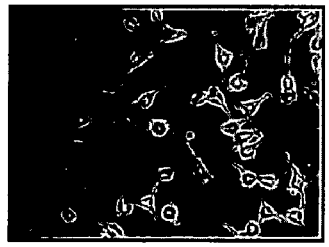
FIG. 11 shows the penetration of the plasmid tagged with rhodamine upon in vitro transfection of NIH-3T3 EWS-Fli1 cells by plasmid-chitosan nanoparticle complexes.
Figure 11B:
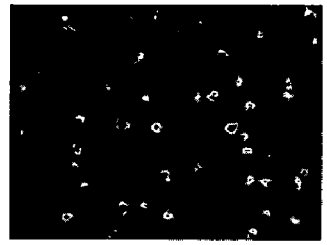
Figure 11C:
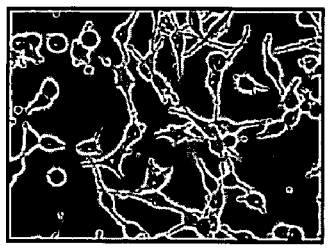
Figure 11D:
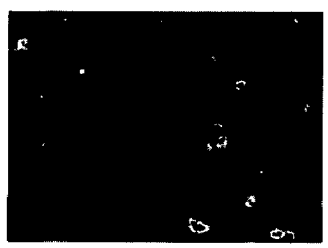

Thirty minutes prior to transfection, the cells were washed with 2 ml of PBS 1× per well then 800 µl of DMEM containing 2% of FCS was added to each well. The complexes (200 µl) were brought into contact with the NIH-33 EWS-Fli1 cells for 16 hours at 37° C. The images of the fluorescent cells are presented in the photograph (FIGS. 11B and 11D).

2. Results
   Fluorescence of the cells was observed when they were coupled to the chitosan nanoparticles (FIGS. 11B and 11D).

Example VIII

Induction of the Expression in Vivo of β-Galactosidase by the Plasmid pCMVβ-gal Vectorized by the Chitosan 5 kDa Nanoparticles 1. Materials and Methods
   a. Treatment of the Animals
   The EWS-Fli1 cells were obtained by transfection of NIH 3T3 cells with the oncogene EWS-Fli1. They were then cultured. When the cells had reached 70% confluence, they were put in suspension in PBS at the concentration of $6.5 \cdot 10^6$ cells/ml. The cells were then inoculated in nude mice via the subcutaneous route at a rate of $1.3 \cdot 10^6$ cells/mouse. Seven days after inoculation of the cells (the tumor had to be visible to the naked eye), the animals were treated either with 100 µl of chitosan 5 kDa nanoparticles (60 µg) associated with 10 µg of plasmid pCMVβ-gal or with 100 µl of plasmid pCMVβ-gal (10 µg). Twenty-four hours after the treatment, the tumors were collected for histological study after immersion in Glyo-Fixx (Shandon).

b. Detection of the Expression of GFP in the Tumor by the Immunohistochemistry Technique
   The tumor fragments were poured into paraffin and labeled by a solution of hematein-eosin-safranin. The protein β-gal was detected on a section of tumor fragment of 4 µm by an anti-β-gal antibody (Clontech) (1:30) and monitored by the Power Vision Histostaining kit (ImmunoVision Technology, CA) after counter-labeling; the samples were observed by microscope (Zeiss) associated with a CDD Camera Imaging System (Sony).

Figure 12A:
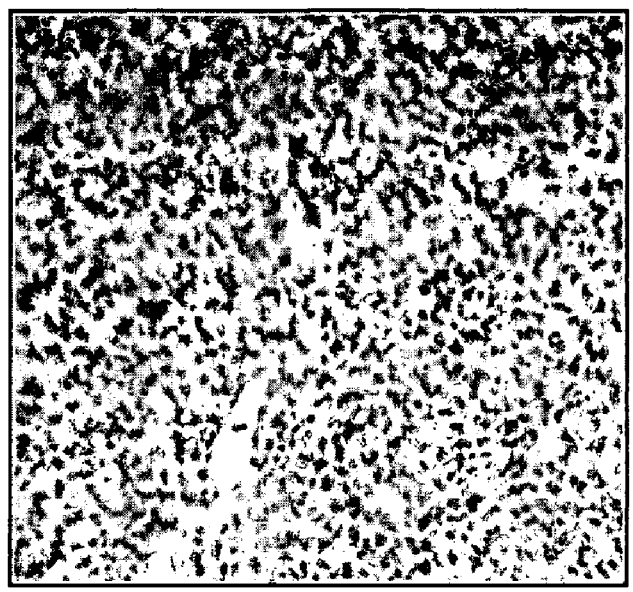
FIG. 12 shows the expression of β-gal in NIH3T3 EWS/Fli-1 cells grafted on nude mice after immunological tagging with anti-β-gal antibodies. (A) transfection with 10 μg of plasmid pCMVβ-gal, (B) transfection with 10 μg of plasmid pCMVβ-gal associated with 60 μg of chitosan 5 kDa nanoparticles.
Figure 12B:
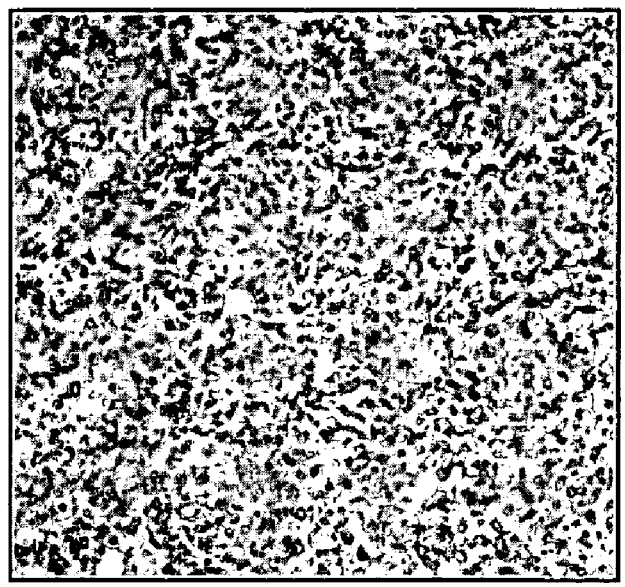

2. Results
   β-gal activity after 24 hours was seen solely when the animals were transfected with the plasmid pCMVβ-gal associated with the chitosan 5 kDa nanoparticles (FIG. 12B) while no β-gal activity was seen when the animals were transfected with the plasmid pCMVβ-gal alone (FIG. 12A).

Example IX

Intracellular Penetration of the Antisense Oligodeoxynucleotides Vectorized by the Chitosan 5 and 10 kDa Nanoparticles in the NIH 3T3 EWS/Fli-1 Cells 1. Materials and Methods
   The NIH 3T3 EWS/Fli-1 cells were sown 24 h prior to their transfection in culture medium without puromycin in culture chambers mounted on plates (Labtek® 4 wells, Nunc Inc.) at the rate of 100,000 cells per well. The cells were rinsed with PBS and incubated for 24 h in 400 µl of OPT1-MEM1 medium supplemented with 2.5% of FCS, 100 U/ml of penicillin and 100 µg/ml of streptomycin in the presence of the different chitosan nanoparticle-oligodeoxy-nucleotides-FITC complexes in the mass ratios of 5:1, 10:1 and 20:1. These complexes were prepared in NaCl 150 mM for a final volume of 100 µl. Two controls were used corresponding on the one hand to the cells incubated with free oligodeoxynucleotides AS-FITC (1 µg) and on the other hand to the cells incubated with 1 nmol of fluorescein (Aldrich). The penetration of the oligodeoxynucleotides AS-FITC into the cells was visualized by confocal microscopy using a Leica TCS NT device (Leica) mounted on an inverted Leica DM IRB/E microscope.

Figure 13A:
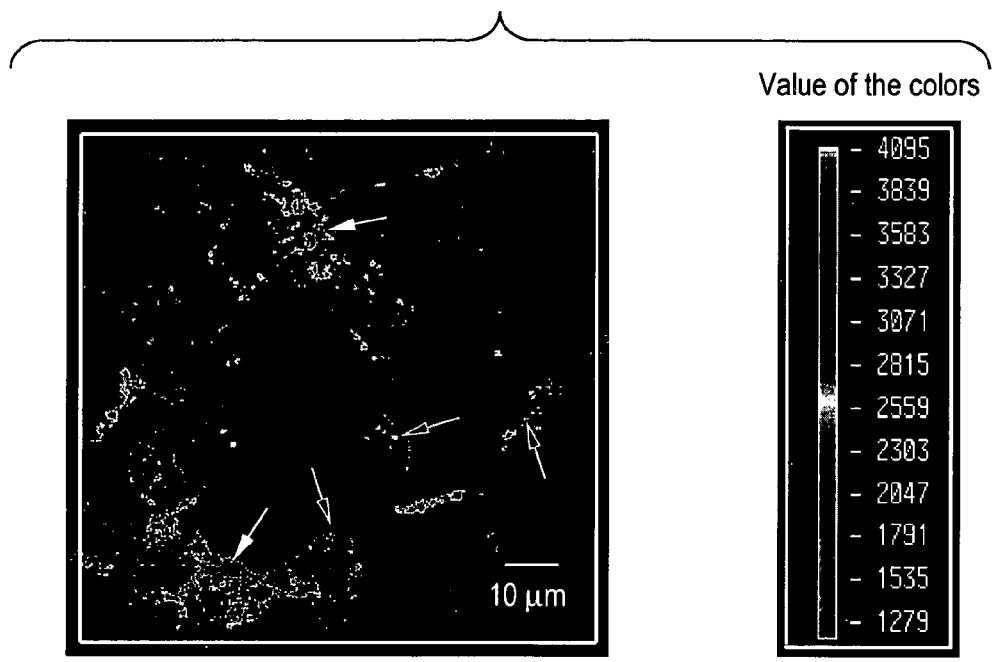
FIG. 13 shows the localization of oligonucleotide EF3008AS-FITC vectorized by chitosan <5 kDa nanoparticles (A) and chitosan 5-10 kDa nanoparticles (B) in NIH 3T3 EWS/Fli-1 cells after observation by confocal microscopy.
Figure 13B:
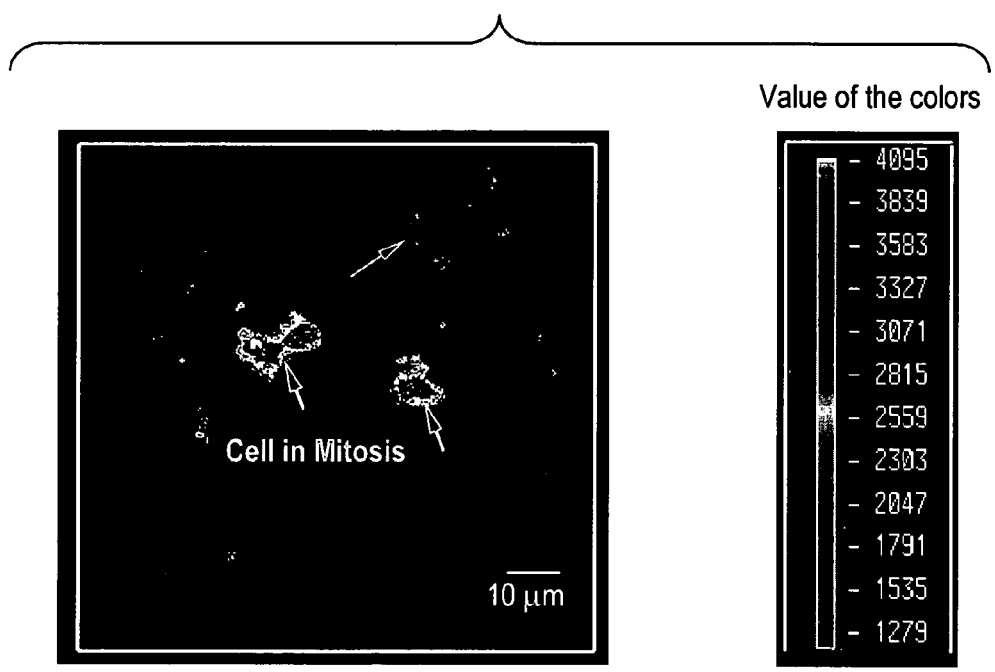
Figure 14A:
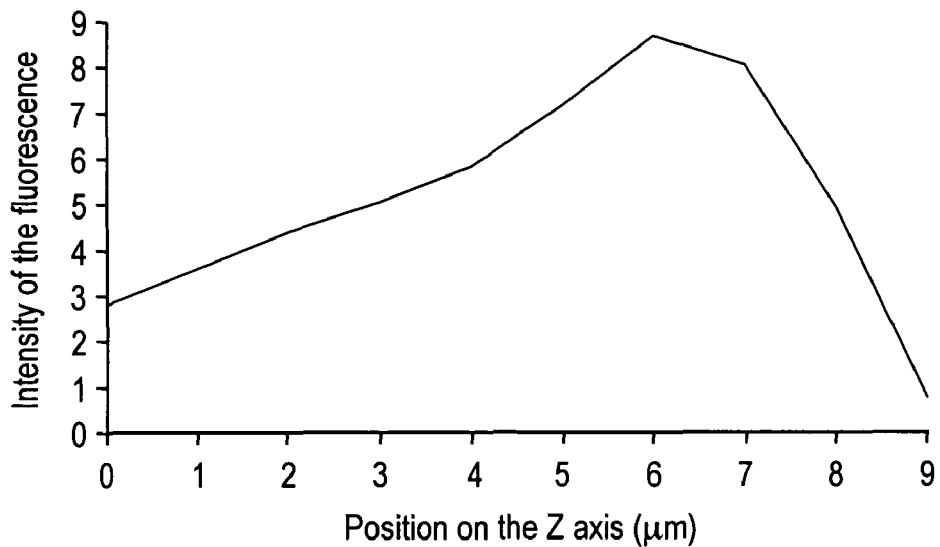
FIG. 14 is a graph showing the intracellular localization of oligonucleotide EF3008AS-FITC vectorized by chitosan <5 kDa nanoparticles (A) and chitosan 5-10 kDa nanoparticles (B) after scanning a field of the cells with the laser of the confocal microscope.
Figure 14B:
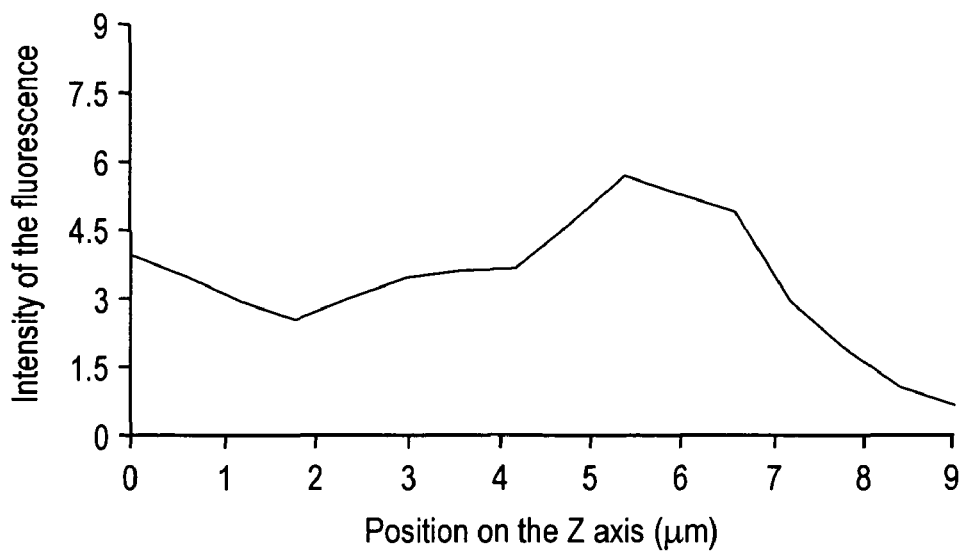

2. Results
   No fluorescent cells were seen after their incubation with FITC alone and the non-vectorized AS-FITC oligodeoxynucleotides. The images of FIG. 13A and FIG. 13B show a field of cells incubated respectively with the complexes chitosan 5 kDa nanoparticles: oligodeoxynucleotides AS-FITC and chitosan 10 kDa nanoparticles: oligodeoxynucleotides AS-FITC in the ratio (5:1). They show that the fluorescence is dispersed in the cytosol when the oligodeoxynucleotides-FITC are vectorized by the chitosan 5 kDa nanoparticles and concentrated at the level of the nucleus in the case of chitosan 10 kDa nanoparticles. The curves of FIGS. 14A and 14B present the sum of the intensities of the fluorescence recorded in the different planes Z of the cell. For a depth of 0 to 1 µm, the fluorescence is located at the level of the apical membrane in the cells. A depth of 8 to 9 µm corresponds to their basal membrane. Between 1 to 8 µm, the fluorescence is localized at the intracellular level. These curves show that for both types of chitosan nanoparticles at the chitosan nanoparticle: oligodeoxynucleotides ratio 5:1, the fluorescence is weakest at the level of the basal membrane of the cells as in the apical membrane exposed to the culture medium containing the oligodeoxynucleotides-FITC. For both types of chitosan at the chitosan nanoparticles:oligodeoxynucleotides ratio (5:1), the fluorescence is primarily localized in the intracellular fraction. These curves confirm that the antisense oligodeoxynucleotides penetrate into the cells. The intensity of fluorescence in the interior of the cells is greater when the oligodeoxynucleotide-FITC is vectorized by chitosan 5 kDa nanoparticles. The cellular localization of the fluorescence is the same for the (10:1) and (20:1) chitosan nanoparticles: oligodeoxynucleotides ratios as for the (5:1) ratio for both types of chitosan nanoparticles.

Example X

Inhibition of Tumor Growth after Intratumoral Administration of Chitosan Nanoparticles to Nude Mice Who Had Developed the Subcutaneous Form of Ewing's Sarcoma 1. Materials and Methods
   Thirty-five female nude mice aged 6-8 weeks were irradiated at 5 gray. Twenty-four hours after the irradiation, the mice received via the subcutaneous route in the right flank 200 µl of a suspension of NIH 3T3 EWS-Fli cells at $5·10^6$ cells/ml in PBS. The animals developed tumors at the end of 14-21 days. Four groups of 7 animals were constituted (PBS group, oligodeoxynucleotide EF3008AS group, chitosan 5 kDa nanoparticles-oligodeoxynucleotide EF3008AS group and chitosan 5 kDa nanoparticles-oligodeoxynucleotide control group. The groups were randomized and the treatment was begun when the tumor reached 2 mm$^3$. The treatment consisted of 5 intratumoral administrations of the products at two-day intervals. The efficacy of the treatments was evaluated by measuring the tumor growth of the treated animals in relation to the controls. The tumor growth was evaluated by the tumor volume (TV). TV was calculated as follows: $TV(mm^3)=a^2 \times b/2$ in which a and b represent respectively the smallest and the largest diameter of the tumor. The statistical analysis of the results was performed with the StatView® computer program (Abacus Concepts, Berkeley, USA).

2. Results

Figure 15:
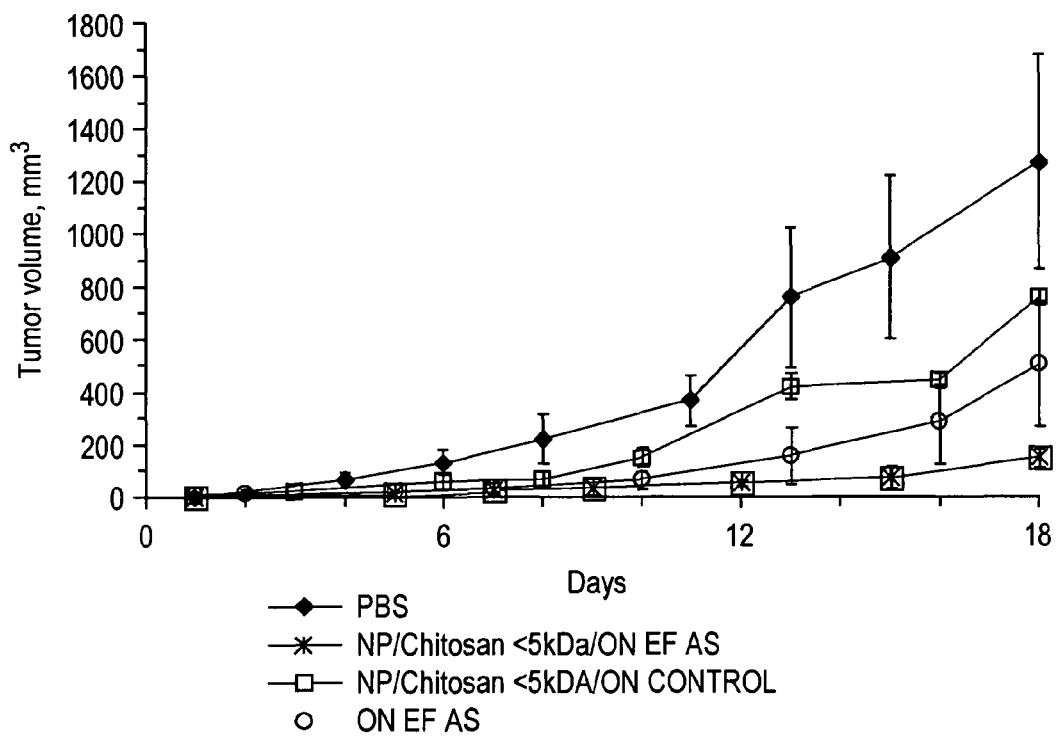
FIG. 15 is a graph showing the inhibition of tumor growth after intratumoral administration: of PBS, chitosan 5 kDa oligodeoxynucleotide EF3008AS nanoparticles, chitosan 5 kDa oligodeoxynucleotide control nanoparticles and oligodeoxynucleotide EF3008AS to irradiated nude mice which had developed a subcutaneous form of Ewing's sarcoma.

The results of inhibition of tumor growth (FIG. 15) show an inhibition of the growth when the animals were treated with oligodeoxynucleotide EF3008AS and the chitosan 5 kDa nanoparticles oligodeoxynucleotide EF3008AS. However, the inhibition of growth was greater when the animals were treated with the chitosan 5 kDa nanoparticles oligodeoxynucleotide EF3008AS compared to the animals who received oligodeoxynucleotide EF3008AS. The control animals which received PBS or control chitosan 5 kDa nanoparticles oligodeoxy-nucleotides exhibited only a slight inhibition of tumor growth.

Example XI

Inhibition of Tumor Growth after Intravenous Administration of the Treatment to Mice which had Developed the Subcutaneous Form of Ewing's Sarcoma 1. Materials and Methods Thirty-six female nude mice aged 6-8 weeks were irradiated at 5 gray. Twenty-four hours after the irradiation, the mice received by the subcutaneous route in the right flank 200 µl of a suspension of EWS-Fli1 cells at $5·10^6$ cells/ml in PBS. The animals developed tumors at the end of 10-20 days. Six groups of 6 animals were constituted: chitosan 5 kDa nanoparticle oligodeoxynucleotide EF3008AS group (ON AS/NP), oligodeoxynucleotide EF3008AS (ON AS), control oligodeoxynucleotide (ON CON), chitosan 5 kDa nanoparticle oligodeoxynucleotide control group (ON CON/NP), chitosan 5 kDa nanoparticles (NP) and NaCl at 0.9% (NaCl). The groups were randomized and the treatment was begun when the tumor reached 10-40 mm$^3$. The treatment consisted of 5 intravenous administrations of the products at intervals of 2 or 3 days. The efficacy of the treatments was evaluated at the end of 15 days by the means of the ratios between the measurements of the tumor volume on day 14 and the measurements of the tumor volume on day 1 of the groups of treated animals in relation to the control groups. The tumor volume was calculated as in example X.

2. Results

Figure 16:
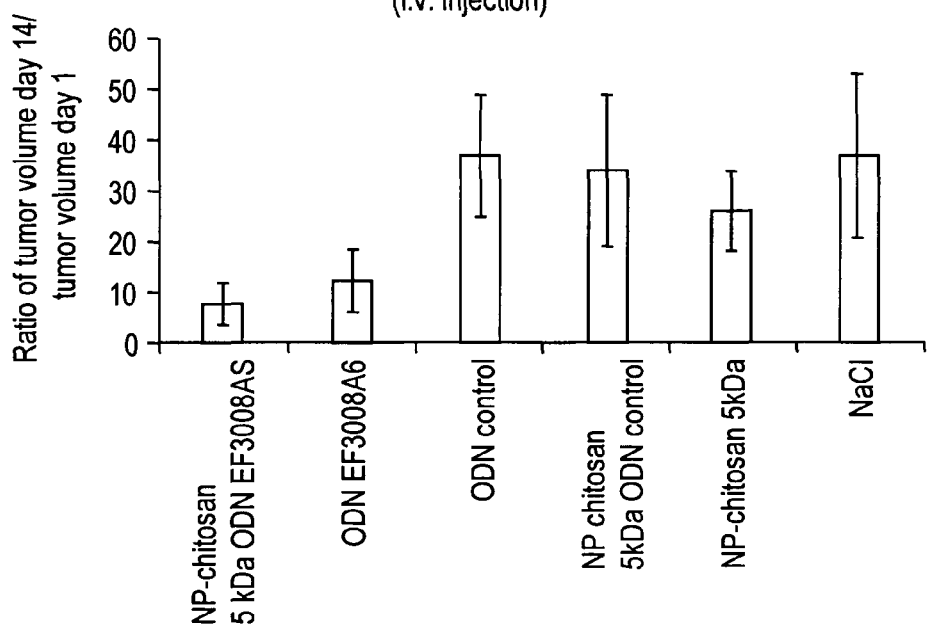
FIG. 16 is a graph showing the inhibition of the tumor growth after intravenous injection of chitosan 5 kDa oligodeoxynucleotide EF3008AS (ON AS/NP) nanoparticles, oligodeoxynucleotide EF3008AS (ON AS), control oligodeoxynucleotide (ON CON), control chitosan 5 kDa oligodeoxynucleotide nanoparticles (ON CON/NP), chitosan 5 kDa nanoparticles (NP) and NaCl to irradiated nude mice which had developed a subcutaneous form of Ewing's sarcoma.

The tumor growth results (FIG. 16) show an inhibition of the growth when the animals were treated with oligodeoxynucleotide EF3008AS (ON AS group) and the chitosan 5 kDa nanoparticles oligodeoxynucleotides EF3008AS (ON AS/NP group). However, there was greater inhibition of the tumor growth when the animals were treated with chitosan 5 kDa nanoparticles oligodeoxynucleotides EF3008AS (ON AS/NP group) compared to the animals who received the oligodeoxynucleotide EF3008AS without chitosan nanoparticles (ON AS group). The animals in the control groups which received NaCl, chitosan nanoparticles alone (NP group) or the control oligodeoxynucleotide with or without chitosan nanoparticles (ON CON/NP and ON CON groups respectively) exhibited only a slight inhibition of the tumor growth.

Example XII

Inhibition of the Expression of the Protein GFP and Inhibition of the Expression of the mRNA of the Protein GFP in Vivo by siRNA Vectorized by the Nanoparticles 1. Materials and Methods Adherent HeLa cells transfected with GFP (HeLa-GFP) in monolayer culture were collected when they reached 70% confluence and put back in suspension in PBS at the rate of $1·10^7$ cells/ml. The cells were then administered via the subcutaneous route in the right flank of nude mice at the rate of $2·10^6$ cells/mouse. Seven days after inoculation of the cells, the animals were distributed in different groups and treated by the intratumoral administration of different preparations in the following manner:

Group 1 (100 µl of a preparation containing 10 µg of double strand GFP oligonucleotide target of siRNA), Group 2 (100 µl of control siRNA alone), Group 3 (100 µl of control siRNA vectorized with 10 µg of chitosan 5 kDa nanoparticles), Group 4 (100 µl of antisense GFP oligonucleotide alone), Group 5 (100 µl of GFP antisense oligonucleotide vectorized by chitosan 5 kDa nanoparticles). Twenty-four hours after the treatment, the tumors were collected and divided into two parts. The part intended for histological study was immersed in a solution of GlyoFixx (Shandon) and the part to be used for the Northern blot test was stored in liquid nitrogen.

a. Detection of the Expression of GFP in the Tumor by the Immunohistochemistry Technique The tumor fragments were poured into paraffin and labeled with a hematein-eosin-safranin solution. GFP was detected on a 4-µm section by an anti-GFP antibody (Clontech) (1:30) and monitored by the PowerVision Histostaining kit (ImmunoVision Technology, CA) after counter-labeling; the samples were observed with a microscope (Zeiss) associated with a CDD Camera Imaging System (Sony).

b. Detection of the Expression of the mRNA of GFP in the Tumor by the Northern Blot Technique The tumor fragments were ground in a solution containing 400 µl of guanidium thiocyanate 4M, 25 mM of N citrate (pH 7), 0.5% of sarcosyl and 0.1M of β-mercaptoethanol at 0° C. After homogenization, the RNA was extracted in phenol as follows: 40 µl of solution of Na acetate 2M (pH 4) was added to 400 µl of H$_2$O saturated with phenol and 120 µl of chloroform:isoamyl alcohol (49:1). The mixture was centrifuged at 1300 rpm for 15 minutes. Then 300 µl of the aqueous phase was precipitated with 300 µl of isopropanol at −20° C. The residue obtained in this manner was washed with ethanol 70%. After drying the residue was taken up with 10 µl of distilled water. Electrophoresis of 2 µg of total RNA was performed on agar gel 1% in MOPS buffer containing 6.3% of formaline. The RNA was transferred onto a nitrocellulose membrane (BA-S85, Schleicher & Shuell) in an SSC buffer (10×). The mRNA of GFP was detected by the Northern blot technique with a fragment of cDNA of GFP of 770 pb labeled by $\alpha^{32}$-P dCTP 300 ci/mM (ICN, France) and Prime-a-gene labeling system (Promega). After washing, the nitrocellulose membrane was analyzed by the Storm 840 phosphorimager (Molecular Dynamic).

2. Results

Figure 17:
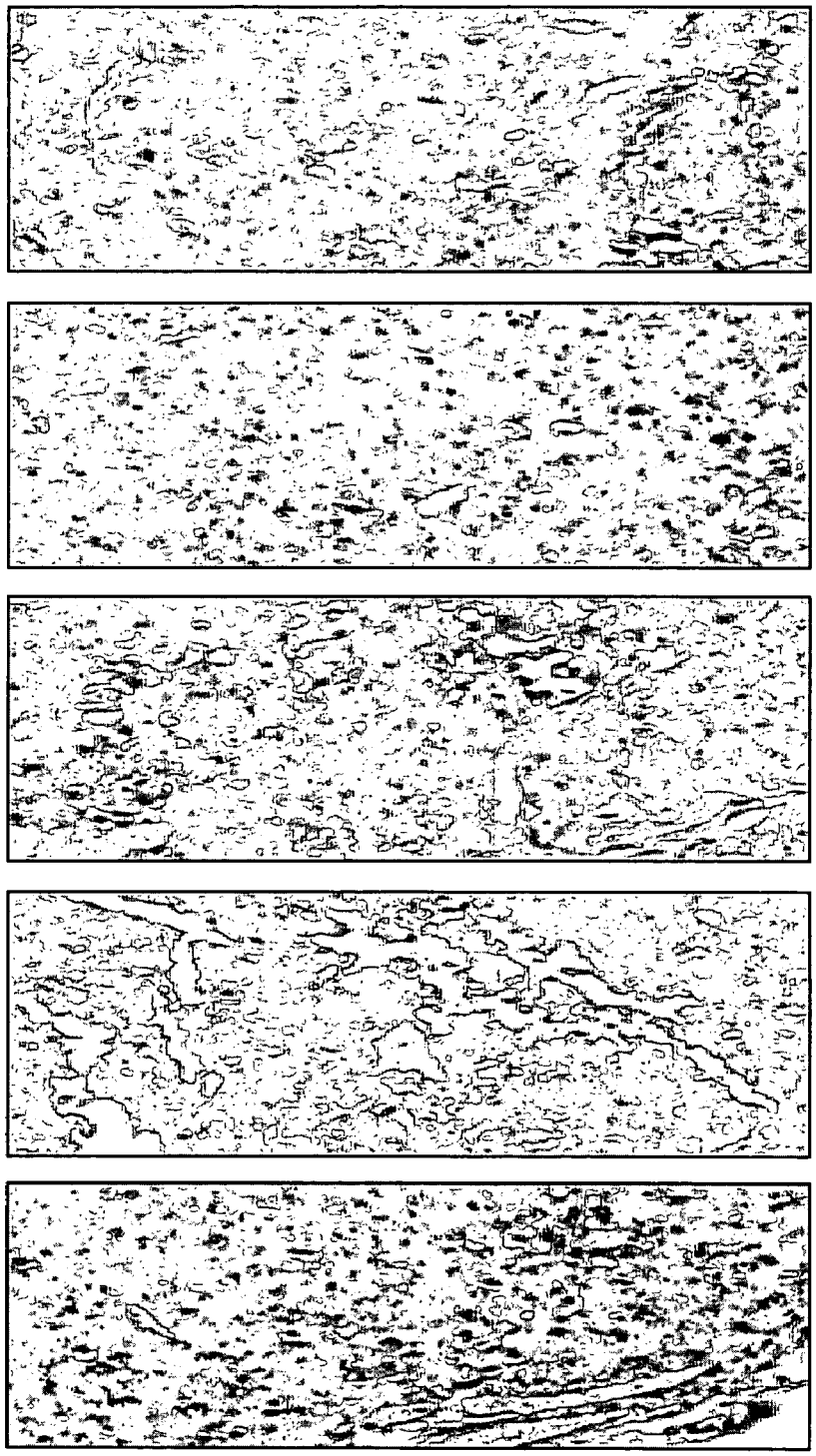
FIG. 17 shows the detection of the expression of the GFP protein in the tumor by the immunohistochemical technique: A (section of the tumor), B (section of the tumor after intratumoral administration of antisense siRNA), C (section of the tumor after intratumoral administration of control siRNA), D (section of the tumor after intratumoral administration of the antisense siRNA vectorized by the chitosan 5 kDa nanoparticles), E (section of the tumor after intratumoral administration of the control siRNA vectorized by the chitosan 5 kDa nanoparticles)
Figure 18:
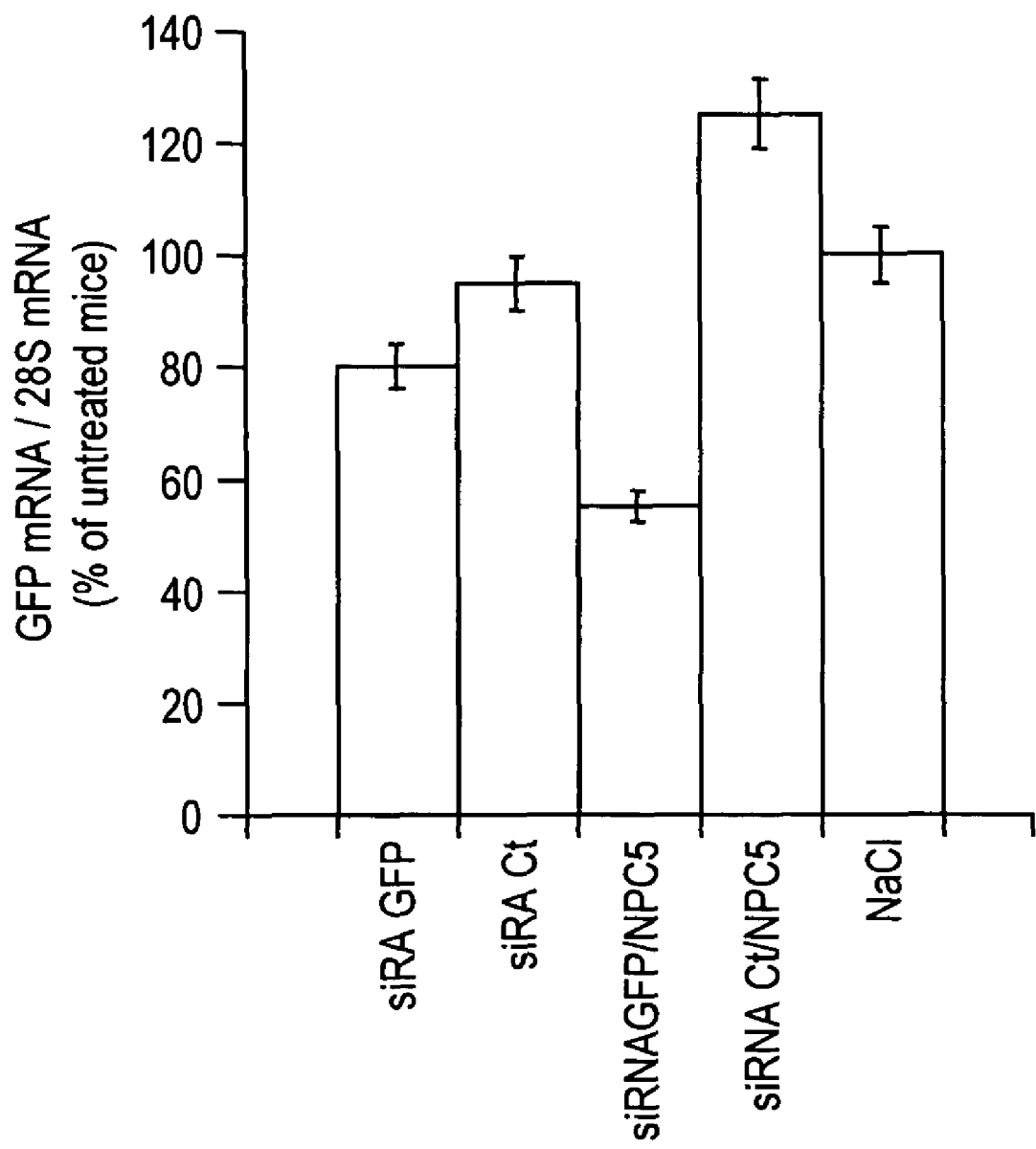
FIG. 18 is a graph showing the detection of the inhibition of the synthesis of the mRNA of the protein GFP by the Northern blot technique. The GFP mRNA was normalized by mRNA 28s.

Inhibition of the synthesis of GFP was seen solely when the siRNA was vectorized with chitosan 5 kDa nanoparticles as shown in FIG. 17D. There was no evidence of inhibition of GFP in any of the other cases (FIGS. 17 A, B, C and E). The antisense activity of siRNA vectorized by the chitosan 5 kDa nanoparticles was confirmed by the Northern blot technique. There can be seen an inhibition of the synthesis of mRNA of GFP of 50% at the end of 24 h when the siRNA was vectorized by the nanoparticles (FIG. 18). These results demonstrate that siRNA vectorized by the nanoparticles interferes with the gene of expression of GFP in vivo.

BIBLIOGRAPHIC REFERENCES

The subject matter of the references set forth below is incorporated herein by reference.

Balassa, L. L., and Grove, B., 1972. U.S. Pat. No. 3,632,754.
Behr, J. P., Demeneix, B., Loeffler, J.-P., Perez-Mutul, J., 1989. Efficient gene transfer into mammalian primary endcrine cells with lipopolyamine-coated DNA. Proc. Natl. Acad. Sci. USA 86, 6982-6986.
Boussif, 0., Lezoualch, F., Zanta, M. A., Mergny, M. D., Scherman, D., Demeneix, B., Behr, J. P., 1995. A versatile vector for gene and oligonucleotide delivery into cells in culture and in vivo: polyethylenimine. Proc. Natl. Acad. Sci. USA 92, 7297-7310.
Chandy, T., and Sharma C. P., 1990. Biomat. Art. Cells. Art. Org., 18, 1.
Chavany, C., Le Doan T., Couvreur, P., Puisieux, F., Helene, C., 1992. Polyalkylcyanoacrylate nanoparticles as polymeric carriers for antisense oligonucleotides, Pharm. Res. 9, 441-449.
Crook, S. T., 1995. Delivery of oligonucleotides and polynucleotides. J. Drug Targeting 3, 185-190.
Douglas, J. T., Curiel, D. T., 1995. Targeted gene therapy. Tumor Targeting 1, 67-84.
Erbacher, P., Zou, S., Bettinger, T., Steffan, A. M., Remy, J. S., 1998, Chitosan-Based Vector/DNA Complexes for Gene Delivery: Biophysical Characteristics and Transfection Ability. Pharm. Res. 15, 1332-1339.
Felgner, P. L., 1990. Particulate systems and polymers for in vitro and in vivo delivery of polynucleotides. Adv. Drug Deliv. Rev. 5, 163-187.
Femandez-Urrusuno, R., Calvo P., Remunan-Lopez, C., Vila-Jato, J. L., and Alonso, M. J. 1999. Enhancement nasal absorption of Insulin Using Chitosan., Pharm. Res., 16, 1576-1581.
Fradet, G., Brister, S., Mulder, D. S., Lough, J., and Averbach, B. L., 1986. In chitin in nature and Technology (R. Muzzarelli, C. Jeuniaux, and G. W. Gooday, eds?), Plenum Press, New York, p. 443.
Fynan, E. F., Webster, R. G., Fuller, D. H., Haynes, J. R., Santoro, J. C., Robinson, H. L., 1993. DNA vaccines: protection immunization by parenteral, mucosal, and gene-gun inoculations. Proc. Natl. Acad. Sci. USA 90, 11478-11482.
Hillyard, I. W., Doczi, J., and Kiernan, P. B., 1964. Proc. Soc. Exp. Biol. Med., 115, 1108.
Hirano, S., Seino, H., Akiyama, Y., and Nonaka, I., 1990. in Progress in Biomedical polymers (C. G. Gebelein and R. L. Dunn, eds), Plenum Press, New York, p. 283.
Kabanov, A. V., Alakhov, V. Y., 1993. Micelles and amphiphilic block copolymers as vehicles for drug delivery. In: Alexandris, P., Lindman, B. (Eds.), Amphiphilic block copolymers: Self Assembly and Applications. Elsevier, Amsterdam, pp. 1-30.
Knapczyk, J., Krowczynski, L., Pawlik, B., and Liber, Z., 1984. In chitin and Chitosan: Sources, Chemistry, Biochemistry, Physical Properties and Applications (G. Skjak-Barek, T. Anthonsen and Sandford P., eds., Elsevier Applied Science, London, p. 665.
Kobayashi, T., Otsuka, S., and Yugari, Y., 1979. Nutr. Rep. Int., 20, 677.
Kreuter, J. Colloidal Drug Delivery Systems, Marcel Decker, New York, 1994, 219-342.
Lasic, D., Templeton, N., 1996. Liposomes in gene therapy. Adv. Drug Deliv. Rev. 20, 221-266.
Ledley, F. D., 1994. Non-viral gene delivery. Curr. Opin. Biotechnol. 5, 626-636.
Morgan, R. A., Anderson, W. F., 1993. Human gene therapy. Arinu. Rev. Biochem. 62, 191-217.
Mumper, R. J., Duguid, J. G., Anwer, K., Barron, M. K., Nitta, H., Rolland, A. P., 1996. polyvinyl derivatives as novel interactive polymers for controlled gene delivery to muscle. Pharm. Res. 13, 701-709.
Calvo, P., Remunan-Lopez, C., Vila-Jato, J. L., Alonso, M. J., 1997. Chitosan and chitosan/ethylene oxidepropylene oxide block copolymer nanoparticles as novel carriers for proteins and vaccines. Pharm. Res. 14, 1431-1436.
Calvo P., Boughaba, A. S., Appel, M., Fattal, E., Alonso, M. J., Couvreur, P., 1998. Oligonucleotide-chitosan nanoparticles as new gene therapy vector. Proceed. $2^{nd}$ World Meeting APGI/APV, Paris, pp. 1111-1112.
Remy, J. S., Abdallah, B., Zanta, M. A., Boussif, 0., Behr, J.-P., Demeneix, B., 1998. Gene transfer with lipospermines and polyethylenimines. Adv. Drug Deliv. Rev. 30, 85-95.
Rha, C. K., Rodriguez-Sanchez, D., and Kienzle-Sterzer, 1984. In Biotechnology of Marine Polysaccharides (R. R. Colwell, E. R. Pariser, A. J. Sinskey, eds.), Hemisphere Plulishing, Washington, p. 284.
Richardson, C. W., Kolbe, H. V. J., Duncan, R., 1999. Potential of low molecular mass Chitosan as a DNA delivery system: biocompatibility, body distribution and ability to complex and protect DNA. Int. J. Pharm., 178, 231-243.
Roberts, G. A. F., 1992. In chitin Chemistry (G. A. F. Roberts ed.), Mac Millan Press, Hounmills, p. 274.
Roberts, G. A. F., in chitin chemistry 1992, (G. A. F. Roberts ed.), Mac Milan Press, Houndmills, p. 1.
Smith, R. L., 1984. U.S. Pat. No. 4,474,769.
Struszczyk, H., Wawro, D., and Niekraszewicz, A., 1991. In Advances in chitin and Chitosan (C. J. Brine, P. A. Sandford, and J. P. Zikakis, eds.), Elsevier Applied Science, London, p. 580.
Tang, M. X., Redmann, C. T., Szoka, F. C., 1996. In vitro gene delivery by degraded polyamidoamine dendrimers. Bioconjugate Chem. 7, 703-714.
Verma, I. M., Somia, N., 1997. Gene therapy-promises, problems and prospects. Nat. Med. 389, 239-242.
Wilson, J. A., Ping, A. J., Krauss, J. C., Mayo-Bond, L., Rogers, C. E., Anderson, D. C., Tod III, R. F., 1990. Correction of CD18 deficient lymphocytes by retrovirus mediated gene transfer. Science, 248, 1413-1416.
Wu, G., Wu, C., 1987. Receptor-mediated in vitro gene transformation by soluble DANN carrier system. J. Biol. Chem. 262, 4429-4432.
Zelphati, O., Szoka, F. C. Jr., 1996. Liposomes as carriers for intracellular delivery of antisense oligonucleotide: real or magic bullet? J. Control. Release 41, 99-119.
Zobel, H. P., Kreuter, J., Werner, D., Noe, C. R., Kumel, G., Zimmer, A., 1997. Cationic polyhexylcyanoacrylate nanoparticles as carriers for antisense oligonucleotide, Antisense Nucleic Acid Drug Dev. 7, 483-493.

Yang, S. C., Ge, H. X., Hu, Y., Jiang, X. Q., Yang, C. Z., 2000. Formation of positively charged poly(butyl cyanoacrylate) nanoparticles stabilized with chitosan, Colloid Polym. Sci. 278, 285-292.

Couvreur, P., Kante, B., Roland, M., Guiot, P., Baudin, P., Speiser, P., 1979. Polycyanoacrylate nanocapsules as potential lysosomotropic carriers: preparation, morphological and sorptive properties. J. Pharm. Pharmacol., 31, 331-332.

The invention claimed is:

1. A vectorization and delivery system of nucleic acid comprising nanoparticles having a substantially homogeneous distribution of size and comprising (i) at least one polymer wherein the polymer is a poly(alkyl cyanoacrylate) in which a linear or branched alkyl group comprises from 1 to 12 carbon atoms, (ii) at least one nontoxic positively charged polysaccharide having a molecular mass lower than 30,000 Da (iii) nucleic acid, wherein the positively charged polysaccharide is chitosan or one of its derivatives.

2. The system according to claim 1, further comprising at least one compound capable of complexing the nucleic acid.

3. The system according to claim 1, wherein the nucleic acid is incorporated or adsorbed at the surfaces of the nanoparticles.

4. The system according to claim 1, wherein the nucleic acid is anionic or comprises an anionic region.

5. The system according to claim 1, wherein the positively charged polysaccharide has a molecular mass of 5,000-30,000 Da.

6. The system according to claim 2, wherein the compound capable of complexing the nucleic acid is a cyclic oligosaccharide.

7. The system according to claim 1, wherein the nucleic acid is selected from among the group consisting of DNA, oligodeoxyribonucleotides, antisense substances and interfering RNAs (siRNA).

8. The system according to claim 1, wherein the nanoparticles have a homogeneous diameter between about 10 and about 300 nm.

9. A method for preparing the system according to claim 1, comprising polymerization of monomers in the presence of the positively charged polysaccharide to obtain a suspension of nanoparticles, wherein said polymerization is carried out at an acid pH between about 2.5 and about 5.

10. The method according to claim 9, wherein the polysaccharide is added at the beginning of polymerization.

11. The method according to claim 9, wherein the acid pH is higher than 3.

12. The method according to claim 9, wherein polymerization is performed in the presence of a polymerization retarder compound which fixes OH groups of the aqueous polymerization medium or the polysaccharide.

13. The method according to claim 9, wherein the amount of polysaccharide is lower than 0.25% and in relation to the weight of the suspension.

14. The method according to claim 9, comprising addition of polyisohexylcyanoacrylate containing $SO_2$ in a solution of citric acid at a pH between 1 and 5 and containing a nonionic surface-active agent, optionally cyclodextrin and chitosan having a molecular weight of 5000-10,000 Da.

15. The method according to claim 9, comprising addition of the nucleic acid at substantially the same time as the polysaccharide.

16. The method according to claim 9, comprising addition of the nucleic acid after formation of the nanoparticles.

17. A suspension of nanoparticles obtained by the method according to claim 9, comprising from about 0.01 to about 5%, of positively charged polysaccharide in relation to the weight of the suspension.

18. The suspension according to claim 17, comprising from about 0.5 to about 50% of nucleic acid in relation to the weight of the suspension.

* * * * *